United States Patent
Sato (10) Patent No.: US 12,022,992 B2
(45) Date of Patent: Jul. 2, 2024

(54) IMAGE SIGNAL PROCESSING DEVICE, IMAGE SIGNAL PROCESSING METHOD, AND PROGRAM

(71) Applicant: OLYMPUS CORPORATION, Tokyo (JP)

(72) Inventor: Tomoya Sato, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 615 days.

(21) Appl. No.: 17/226,250

(22) Filed: Apr. 9, 2021

(65) Prior Publication Data

US 2021/0251467 A1    Aug. 19, 2021

Related U.S. Application Data

(63) Continuation of application No. PCT/JP2018/037646, filed on Oct. 10, 2018.

(51) Int. Cl.
    *A61B 1/00*      (2006.01)
    *A61B 1/06*      (2006.01)

(52) U.S. Cl.
    CPC .... *A61B 1/000095* (2022.02); *A61B 1/00006* (2013.01); *A61B 1/0005* (2013.01); *A61B 1/0655* (2022.02)

(58) Field of Classification Search
    CPC ............ A61B 1/000095; A61B 1/0655; A61B 1/00006; A61B 1/0005
See application file for complete search history.

(56) References Cited

U.S. PATENT DOCUMENTS

| | | | |
|---|---|---|---|
| 6,990,249 B2 * | 1/2006 | Nomura | H04N 1/00135 |
| | | | 348/580 |
| 7,177,481 B2 * | 2/2007 | Kaji | H04N 1/407 |
| | | | 382/265 |

(Continued)

FOREIGN PATENT DOCUMENTS

| | | |
|---|---|---|
| JP | 2007-048104 A | 2/2007 |
| JP | 2012-147052 A | 8/2012 |

(Continued)

OTHER PUBLICATIONS

Dec. 25, 2018 International Search Report issued in Application No. PCT/JP2018/037646.

(Continued)

*Primary Examiner* — John J Lee
(74) *Attorney, Agent, or Firm* — Oliff PLC (57) ABSTRACT

An image signal processing device includes: a base component extractor that generates an original base component signal; a base component adjuster that generates a first base component signal by performing weighted average processing; a detail component extractor that generates a first detail component signal based on the first base component signal; a relative emphasizer that outputs a second base component signal and a second detail component signal by relatively emphasizing the first detail component signal to the first base component signal; a combiner that generates a combined image signal by combining the second base component signal and the second detail component signal; and a storage that stores control parameters regarding similarity between the image signal and the first base component signal. The base component adjuster generates the first base component signal by performing the weighted average processing by using a weight coefficient determined in accordance with selected control parameter.

9 Claims, 6 Drawing Sheets

(56) References Cited

U.S. PATENT DOCUMENTS

| | | | | |
|---|---|---|---|---|
| 2013/0060488 A1* | 3/2013 | Ghabour | ................. | G06T 11/00 |
| | | | | 702/38 |
| 2018/0344136 A1* | 12/2018 | Kikuchi | ............. | G02B 23/2484 |
| 2019/0058844 A1 | 2/2019 | Sato | | |
| 2019/0328218 A1 | 10/2019 | Sato | | |

FOREIGN PATENT DOCUMENTS

| | | |
|---|---|---|
| JP | 2012-230635 A | 11/2012 |
| WO | 2017-104291 A1 | 6/2017 |
| WO | 2017-203866 A1 | 11/2017 |
| WO | 2018-150627 A1 | 8/2018 |

OTHER PUBLICATIONS

Jun. 21, 2022 Office Action issued in Chinese Patent Application No. 2020-551081.
Jun. 21, 2022 Office Action issued in Japanese Patent Application No. 2020-551081.

\* cited by examiner

PIXEL POSITION

Fig.5

PIXEL POSITION

IMAGE SIGNAL PROCESSING DEVICE, IMAGE SIGNAL PROCESSING METHOD, AND PROGRAM

CROSS REFERENCE TO RELATED APPLICATIONS

This is a Continuation Application of PCT Application No. PCT/JP2018/037646, filed Oct. 10, 2018, which was not published under PCT Article 21(2) in English.

BACKGROUND

An endoscope system, which enables early detection and early treatment of diseases, has recently been increasingly used mainly in the medical field. There are a variety of types of diseases to be detected by endoscopy, which include, for example, less visible diseases such as inflammation and unevenness in the gastric mucosa. To detect such a less visible disease without overlook, a technology for improving the visibility of diseases has been required in the field of endoscope systems.

A technology related to such a technical problem is described in, for example, International Publication No. WO 2017/203866. International Publication No. 2017/203866 describes a technology in which an endoscopic image is generated by dividing a video signal into a base component and a detail component, performing gradation compression processing on the base component, and combining the detail component and the base component subjected to the gradation compression processing. It should be noted that the detail component contains a contrast component containing information such as an outline and a texture of an object.

The technology described in International Publication No. 2017/203866 allows for obtaining an endoscopic image with a favorable visibility, which makes it possible to detect a disease more easily. Further, the technology described in International Publication No. 2017/203866 allows for improving the visibility of an endoscopic image with a color less changed. This makes it possible to diagnose a disease on the basis of already established pathognomy as ever.

SUMMARY

This disclosure relates to an image signal processing device, an image signal processing method, and a program.

An image signal processing device according to an aspect of the present invention includes: a base component extractor that generates an original base component signal by extracting a base component from an image signal; a base component adjuster that generates a first base component signal by performing weighted average processing on the image signal and the original base component signal; a detail component extractor that generates a first detail component signal by extracting a detail component from the image signal based on the first base component signal; a relative emphasizer that outputs a second base component signal and a second detail component signal by performing signal processing on at least one of the first base component signal and the first detail component signal, the signal processing relatively emphasizing the first detail component signal with respect to the first base component signal; and a combiner that generates a combined image signal by combining the second base component signal and the second detail component signal.

An image signal processing device according to another aspect of the present invention includes: a divider that divides an image signal into a first base component signal and a first detail component signal in accordance with a control parameter and outputs the first base component signal and the first detail component signal; a relative emphasizer that outputs a second base component signal and a second detail component signal by performing signal processing on at least one of the first base component signal and the first detail component signal, the signal processing relatively emphasizing the first detail component signal with respect to the first base component signal; and a combiner that generates a combined image signal by combining the second base component signal and the second detail component signal.

An image signal processing device according to sill another aspect of the present invention includes: a base component extractor that generates an original base component signal by extracting a base component from an image signal; a base component adjuster that generates a first base component signal by performing weighted average processing on the image signal and the original base component signal; a detail component extractor that generates a first detail component signal by extracting a detail component from the image signal based on the first base component signal; a relative emphasizer that outputs a second base component signal and a second detail component signal by performing signal processing on at least one of the first base component signal and the first detail component signal, the signal processing relatively emphasizing the first detail component signal with respect to the first base component signal; and a combiner that generates a combined image signal by combining the second base component signal and the second detail component signal. The relative emphasizer includes a gradation compressor that generates the second base component signal by performing gradation compression processing on any one of the image signal, the original base component signal, or the first base component signal.

An image signal processing method according to an aspect of the present invention includes: generating an original base component signal by extracting a base component from an image signal; generating a first base component signal by performing weighted average processing on the image signal and the original base component signal; generating a first detail component signal by extracting a detail component from the image signal based on the image signal and the first base component signal; outputting a second base component signal and a second detail component signal by performing signal processing on at least one of the first base component signal and the first detail component signal, the signal processing relatively emphasizing the first detail component signal with respect to the first base component signal; and generating a combined image signal by combining the second base component signal and the second detail component signal.

A program according to an aspect of the present invention causes a computer to perform processing including: generating an original base component signal by extracting a base component from an image signal; generating a first base component signal by performing weighted average processing on the image signal and the original base component signal; generating a first detail component signal by extracting a detail component from the image signal based on the image signal and the first base component signal; outputting a second base component signal and a second detail component signal by performing signal processing on at least one of the first base component signal and the first detail component signal, the signal processing relatively empha- sizing the first detail component signal with respect to the first base component signal; and generating a combined image signal by combining the second base component signal and the second detail component signal.

DETAILED DESCRIPTION

The technology described in International Publication No. 2017/203866 causes a detail component to be relatively emphasized with respect to a base component as a result of gradation compression of the base component. If such a relative emphasis is excessively strong, the impression of an obtained endoscopic image is considerably different from that of a typical endoscopic image in some cases. This would cause cases such as diagnosing the degree of inflammation in the gastric mucosa as being higher than an actual degree, although a disease is easily detected with an improved visibility. Accordingly, a technology to adjust the degree of a relative emphasis to adjust the impression of an image has been required.

In light of the above, description will be made on embodiments of the present invention.

Figure 1:
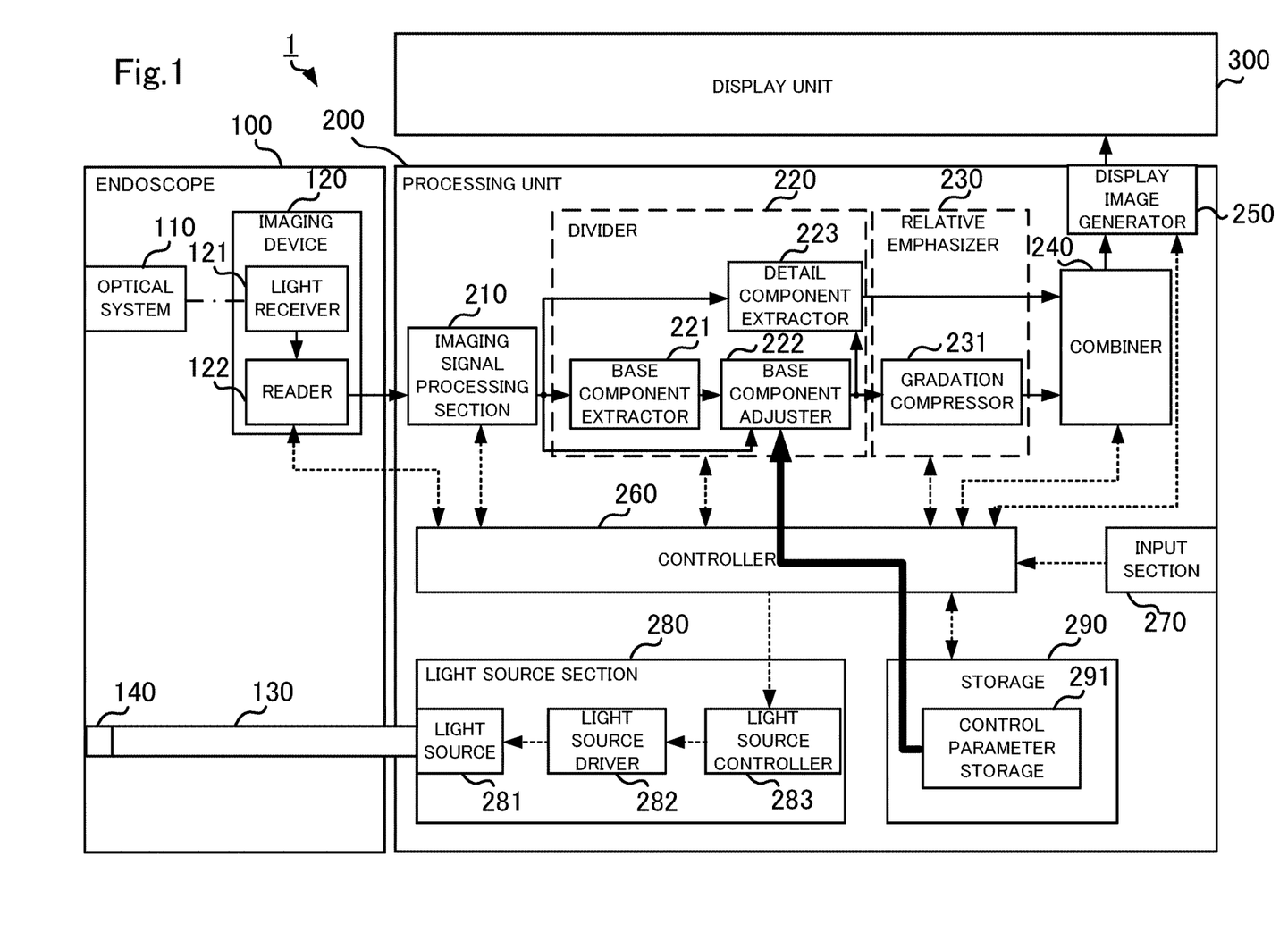
FIG. 1 shows an example of a configuration of an endoscope system 1 according to an exemplary embodiment.

FIG. 1 shows an example of a configuration of an endoscope system 1 according to the present embodiment. The endoscope system 1, which is, for example, a medical endoscope system, includes an endoscope 100, a processing device 200, and a display device 300 as shown in FIG. 1.

The endoscope 100, which is, for example, a flexible endoscope, includes an insertion section being inserted into an object, an operation section being operated by an operator, a universal cord section extending from the operation section, and a connector section provided at an end of the universal cord section and that is to be connected to the processing device 200. The endoscope 100 outputs an imaging signal, which is generated by capturing an image of an object with the insertion section inserted in a body cavity of the object, to the processing device 200.

The endoscope 100 includes an optical system 110, an imaging device 120, a light guide 130, and an illumination lens 140. It should be noted that the optical system 110, the imaging device 120, and the illumination lens 140 are provided in the insertion section, and the light guide 130 is disposed from the connector section to the insertion section through the universal cord section and the operation section.

The optical system 110, which includes one or more lenses, collects light from an object, forming an optical image of the object on a light receiver 121 of the imaging device 120. The optical system 110 may also include a motion structure that causes at least a part of the one or more lenses of the optical system 110 to move in an optical axis direction. By virtue of the motion structure, the optical system 110 may implement an optical zoom function to change the projection magnification of an optical image and a focus function to move a focal position to put a focus on an object.

The imaging device 120 is, for example, a two-dimensional image sensor such as a CCD (Charge Coupled Device) image sensor or a CMOS (Complementary Metal Oxide Semiconductor) image sensor. The imaging device 120 receives light from an object on a light-receiving surface through the optical system 110 and converts the received light to an electric signal, thereby generating an imaging signal of the object. In more detail, the imaging device 120 includes the light receiver 121 and a reader 122.

In the light receiver 121, for example, a plurality of pixels including respective photodiodes and capacitors are two-dimensionally arranged. The pixels may also include respective color filters. The color filters arranged in the plurality of pixels may be arranged in, for example, a Bayer arrangement. Alternatively, the pixels may include respective plurality of photodiodes stacked in a thickness direction in place of the color filters. The reader 122 reads electric signals generated by photoelectric conversion from the plurality of pixels and outputs the electric signals as imaging signals to the processing device 200.

The light guide 130 guides illumination light delivered from a light source section 280 of the processing device 200 to the illumination lens 140. The illumination lens 140 irradiates an object with the illumination light from the light guide 130.

The processing device 200 is a control device that controls an operation of the endoscope system 1 and is referred to also as an endoscope processor. The processing device 200, which is an example of an image signal processing device, for example, performs later-described signal processing on an imaging signal outputted from the endoscope 100, generates an image signal for display, and causes an image of an object to be displayed on the display device 300. In addition to the above, the processing device 200 performs a variety of processing such as light quantity control.

The processing device 200 includes a divider 220, a relative emphasizer 230, and a combiner 240. The processing device 200 may also include an imaging signal processing section 210, a display image generator 250, a controller 260, an input section 270, the light source section 280, and a storage 290. It should be noted that the imaging signal processing section 210, the divider 220, the relative emphasizer 230, the combiner 240, the display image generator 250, the controller 260, and the light source section 280 may each include, for example, a general-purpose processor such as a CPU or may each include a dedicated processor such as an ASIC or an FPGA.

In other words, the processing device 200 includes electric circuitry that implements the above-described components.

In the processing device 200, the divider 220 divides the image signal generated by the imaging signal processing section 210 into a base component signal and a detail component signal. Subsequently, in the processing device 200, the relative emphasizer 230 relatively emphasizes the detail component signal with respect to the base component signal and then the combiner 240 combines these signals to generate a combined image signal. Further, in the processing device 200, the display image generator 250 generates an image signal for display from the combined image signal to cause an endoscopic image to be displayed on the display device 300. The controller 260 collectively controls these operations. Further, the controller 260 reads, in response to input from the input section 270, a control parameter used for division processing from the storage 290 and provides the control parameter to the divider 220. Further, the controller 260 also controls automatic light quantity control performed by the light source section 280.

It should be noted that the base component signal refers to a signal corresponding to, among image components contained in the image signal, a base component. Similarly, the detail component signal refers to a signal corresponding to, among the image components contained in the image signal, a detail component.

Further, the base component is a component that is less correlated with visual perception than the detail component. The base component is also a low-frequency component with a low spatial frequency while being an illumination light component that is dependent on the illumination light for irradiating an object. In contrast, the detail component is more correlated with visual perception than the base component. The detail component is also a high-frequency component with a high spatial frequency while being a reflectance component that is dependent on a reflectance of an object.

The imaging signal processing section 210 generates an image signal by performing predetermined processing on an imaging signal received from the endoscope 100. The predetermined processing includes, for example, denoising processing, analog-digital conversion processing, OB subtraction processing, WB correction processing, demosaicing processing, color matrix processing, etc. The imaging signal processing section 210 outputs the generated image signal to the divider 220.

The divider 220 divides the image signal received from the imaging signal processing section 210 into a base component signal and a detail component signal in accordance with a control parameter. In more detail, the divider 220 includes a base component extractor 221, a base component adjuster 222, and a detail component extractor 223.

It should be noted that hereinafter, the base component signal outputted from the divider 220 is referred to as, in particular, a first base component signal and the detail component signal outputted from the divider 220 is referred to as, in particular, a first detail component signal. Similarly, the base component signal outputted from the relative emphasizer 230 is referred to as, in particular, a second base component signal and the detail component signal outputted from the relative emphasizer 230 is referred to as, in particular, a second detail component signal.

The base component extractor 221 generates a base component signal by extracting the base component from the image signal received from the imaging signal processing section 210 and outputs the base component signal to the base component adjuster 222. The base component signal generated by the base component extractor 221 is hereinafter referred to as, in particular, an original base component signal. Although a method of extracting the base component is not limited, for example, an edge preserving smoothing filter such as a bilateral filter or an epsilon filter may be used.

The base component adjuster 222 generates the first base component signal by performing weighted average processing on the image signal and the original base component signal. In more detail, the base component adjuster 222 generates the first base component signal by acquiring a control parameter that specifies similarity between the image signal and the first base component signal from the storage 290 and then performing the weighted average processing by using weight coefficients determined in accordance with the control parameter. The generated first base component signal is outputted to the detail component extractor 223 and the relative emphasizer 230. It should be noted that the weighted average processing performed by the base component adjuster 222 is, for example, alpha blend processing. The control parameter used by the base component adjuster 222 is, for example, an alpha value α used for the alpha blend processing. The weight coefficients determined in accordance with the control parameter are, for example, a weight coefficient α for the image signal and a weight coefficient (1−α) for the original base component signal.

The weighted average processing performed by the base component adjuster 222 is processing for generating a signal between the original base component signal and the image signal, substantially, processing for approximating the original base component signal to the image signal inputted to the divider 220. The degree of the approximation to the image signal can be adjusted by the control parameter. In other words, the weighted average processing performed by the base component adjuster 222 is processing for approximating the original base component signal to the image signal inputted to the divider 220 in accordance with the control parameter.

The detail component extractor 223 generates the first detail component signal by extracting the detail component from the image signal on the basis of the first base component signal. In more detail, the detail component extractor 223 generates the first detail component signal by dividing the image signal by the first base component signal. The generated first detail component signal is outputted to the combiner 240 via the relative emphasizer 230.

The relative emphasizer 230 outputs the second base component signal and the second detail component signal to the combiner 240 by performing, on the first base component signal outputted from the divider 220, signal processing for relatively emphasizing the first detail component signal with respect to the first base component signal. In more detail, the relative emphasizer 230 includes a gradation compressor 231.

The gradation compressor 231 generates the second base component signal by performing gradation compression processing on the first base component signal received from the base component adjuster 222 and outputs the second base component signal to the combiner 240. A method for gradation compression processing performed by the gradation compressor 231 is not limited. Any method in which a dynamic range of the base component signal is compressed at a predetermined ratio is acceptable and a method similar to gradation compression processing being performed on a typical endoscopic image may be used.

The gradation compressor 231 performs the gradation compression processing on the first base component signal, thereby relatively emphasizing the first detail component signal with respect to the first base component signal. It should be noted that the second base component signal outputted from the relative emphasizer 230 is a signal resulting from performing the gradation compression processing on the first base component signal. In contrast, the second detail component signal outputted from the relative emphasizer 230 is the same as the first detail component signal.

The combiner 240 generates the combined image signal by combining the second base component signal and the second detail component signal and outputs the combined image signal to the display image generator 250. In more detail, the combiner 240 generates the combined image signal by multiplying the second base component signal and the second detail component signal.

The display image generator 250 generates the image signal for display from the combined image signal received from the combiner 240 and outputs the image signal for display to the display device 300.

The controller 260 collectively controls the operations of the components in the processing device 200. The controller 260 also outputs a control signal to a device (for example, the imaging device 120) outside the processing device 200 to control an operation of the external device.

The input section 270, which is, for example, a switch, a touch panel, a mouse or the like provided in the processing device 200, outputs a signal corresponding to an operation by operator to the controller 260. It should be noted that the input section 270 may be circuitry that receives a signal from an input device connected to the processing device 200, such as a keyboard, a mouse, or a joystick, or may be circuitry that receives a signal from an input terminal such as a tablet computer.

The light source section 280 outputs the illumination light for irradiating an object through the endoscope 100. In more detail, the light source section 280 includes a light source 281, a light source driver 282, and a light source controller 283.

The light source 281 is a light source that emits the illumination light being delivered to the endoscope 100. The light source 281 is, for example, an LED light source without limitation but may be a lump light source such as a xenon lamp or a halogen lamp or a laser light source. Further, the light source 281 may include a plurality of LED light sources that emit respective illumination lights different in color.

The light source driver 282 is a driver that drives the light source 281, for example, a LED driver. The light source driver 282 drives the light source 281 in accordance with an instruction value (for example, a current value, a voltage value) from the light source controller 283.

The light source controller 283 outputs the instruction value to the light source driver 282 on the basis of a control signal from the controller 260, thereby controlling illumination light intensity and illumination timing.

The storage 290 includes a ROM, a RAM, a hard disk, a flash memory, etc. The storage 290 stores various programs used by the endoscope system 1, parameters, and data obtained by the endoscope system 1. In more detail, the storage 290 includes a control parameter storage 291 that stores at least the control parameter used for the division processing by the divider 220.

The display device 300 is a device that displays an endoscopic image by using the image signal for display received from the processing device 200. The display device 300 is, for example, a display such as a liquid crystal display or an organic EL display.

In the endoscope system 1 configured as described above, the relative emphasizer 230 of the processing device 200 relatively emphasizes the detail component signal with respect to the base component signal, which makes it possible to obtain an endoscopic image having a higher visibility than ever before. Further, the divider 220 of the processing device 200 can adjust the similarity between the base component signal and the input signal, which makes it possible to adjust a difference in impression from a typical endoscopic image.

The processing device 200 can thus improve visibility with respect to a typical endoscopic image and adjust a difference in impression from the typical endoscopic image. Further, the endoscope system 1 including the processing device 200 can display an endoscopic image with an improved visibility and an adjusted impression. This allows for reliable detection of a disease and accurate diagnosis of the detected disease.

Figure 2:
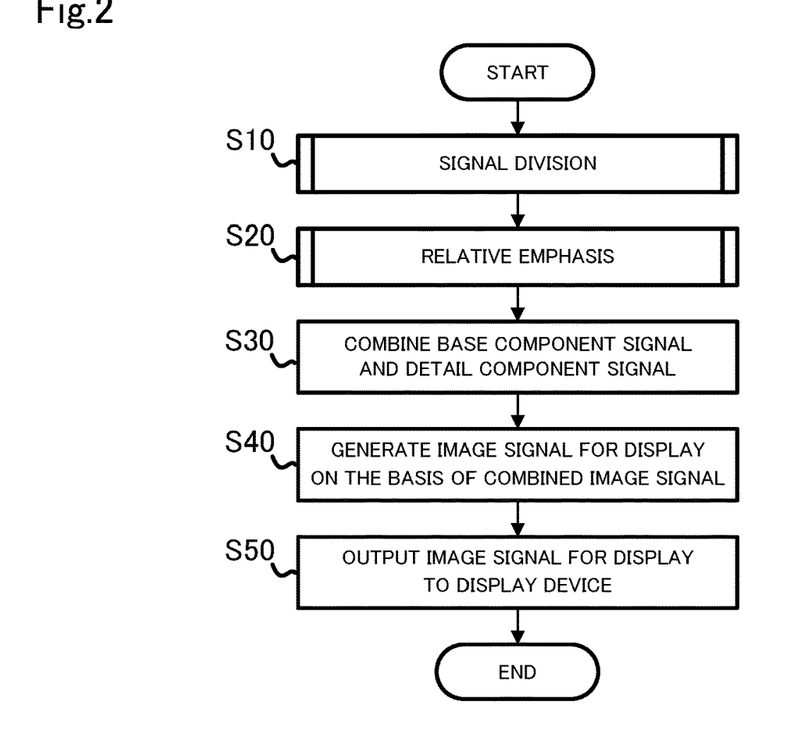
FIG. 2 is a flowchart of image signal processing according to an exemplary embodiment.
Figure 3:
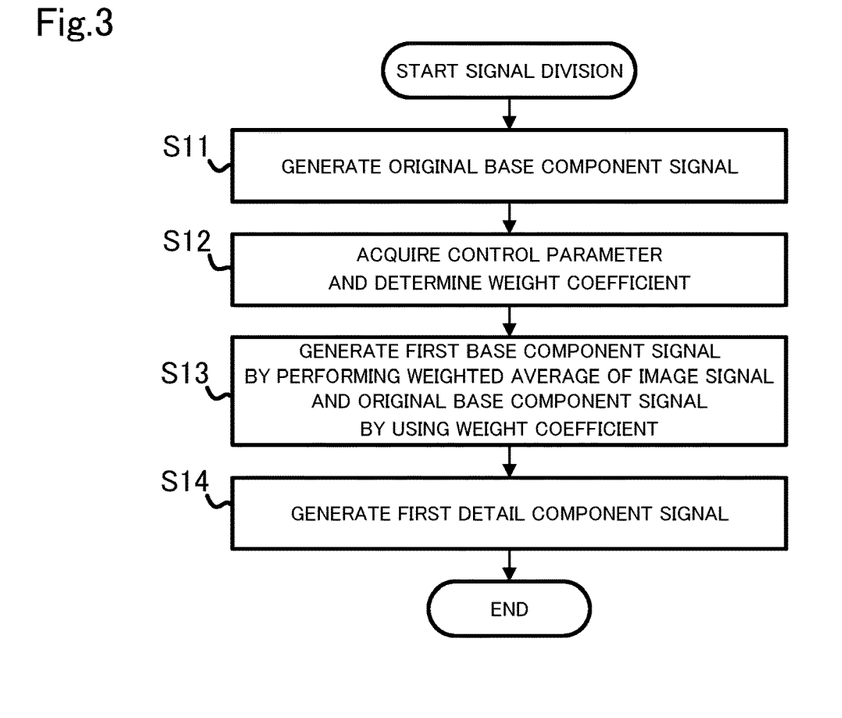
FIG. 3 is a flowchart of signal division processing according to an exemplary embodiment.
Figure 4:
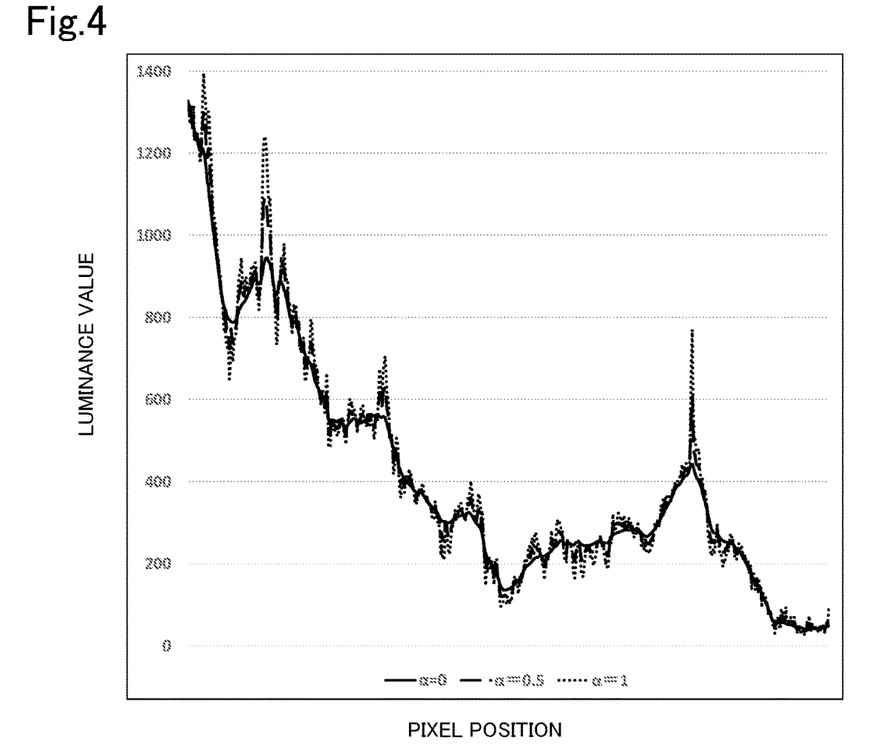
FIG. 4 shows a line profile regarding a base component signal at each of alpha values of 0, 0.5, and 1.
Figure 5:
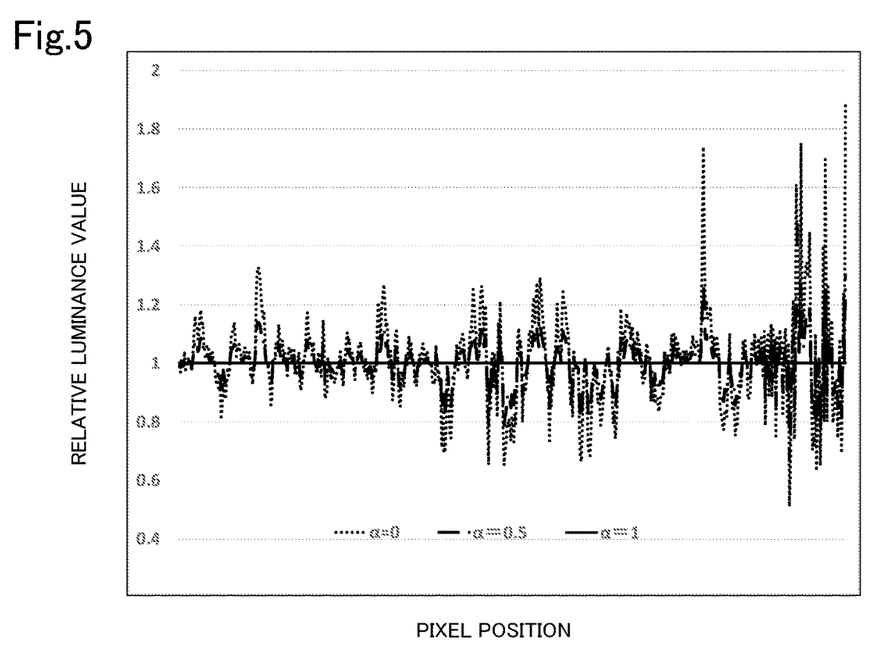
FIG. 5 shows a line profile regarding a ratio between a detail component signal and a base component signal at each of alpha values of 0, 0.5, and 1.

FIG. 2 is a flowchart of image signal processing according to the present embodiment. FIG. 3 is a flowchart of signal division processing according to the present embodiment. FIG. 4 shows a line profile regarding a base component signal at each of alpha values of 0, 0.5, and 1. FIG. 5 shows a line profile regarding a ratio between a detail component signal and a base component signal at each of alpha values of 0, 0.5, and 1. A specific description will be made below on an image signal processing method performed by the processing device 200 with reference to FIG. 2 to FIG. 5.

The processing device 200 performs, in response to receiving an imaging signal from the endoscope 100, the signal division processing on an image signal generated on the basis of the imaging signal (step S10). It should be noted that description will be made hereinbelow on an example where the processing device 200 is connected to the endoscope 100 and performs the signal division processing in response to receiving an imaging signal from the endoscope 100; however, the signal division processing may be performed in response to, for example, reading an image signal from the storage 290.

When the signal division processing shown in FIG. 3 is started, the processing device 200 first generates an original base component signal (step S11). Here, for example, the base component extractor 221 extracts a base component from the image signal by performing, on the image signal, filtering processing with an edge preserving smoothing filter.

Next, the processing device 200 acquires a control parameter to determine a weight coefficient (step S12). Here, for example, the base component adjuster 222 first reads a control parameter, i.e., the alpha value a, from the control parameter storage 291. It should be noted that the alpha value a, which is a value in a range from 0 to 1, is determined in advance in accordance with selection by an operator. Subsequently, the base component adjuster 222 determines the weight coefficient by using the alpha value a. Specifically, the base component adjuster 222 determines, for example, $\alpha$ as a weight coefficient for the image signal and $(1-\alpha)$ as a weight coefficient for the original base component signal.

The processing device 200 performs, in response to determination of the weight coefficients, weighted averaging of the image signal and the original base component signal by using the weight coefficients, generating a first base component signal (step S13). Here, for example, the base component adjuster 222 generates the first base component signal by performing the following alpha blend processing. In this case, with the alpha value a being closer to 1, the first base component signal is further approximated to the image signal.

$$\text{first base component signal} = \alpha \times \text{image signal} + (1-\alpha) \times \text{original base component signal} \quad (1)$$

FIG. 4 shows a line profile regarding the first base component signal at each of $\alpha=0$, $\alpha=0.5$, and $\alpha=1$. The abscissa axis represents pixel positions and the ordinate axis represents luminance values of the first base component signal at the pixel positions.

As is apparent from the expression (1), the first base component signal at $\alpha=1$ is the very same as the image signal and the first base component signal at $\alpha=0$ is the very same as the original base component signal. Thus, as shown in FIG. 4, the first base component signal at α=0 becomes a signal with a high-frequency component removed by smoothing processing, whereas, at α=1, becoming a signal that considerably varies in luminance value with the pixel positions. Further, at α=0.5, the first base component signal becomes an intermediate signal between these signals.

With the first base component signal being generated, the processing device 200 generates a first detail component signal (step S14), terminating the signal division processing. Here, for example, the detail component extractor 223 generates the first detail component signal by dividing the image signal by the first base component signal generated in step S13.

FIG. 5 shows a line profile regarding a ratio of the first detail component signal to the first base component signal at each of α=0, α=0.5, and α=1. The abscissa axis represents pixel positions and the ordinate axis represents relative luminance values of the first detail component signal with respect to the first base component signal at the pixel positions.

As shown in FIG. 5, the relative luminance value becomes a value considerably separate from 1 at α=0, whereas the relative luminance value is fixed to 1 at α=1. Further, at α=0.5, the relative luminance value exhibits intermediate characteristics between those of these values.

In response to termination of the signal division processing, the processing device 200 performs relative emphasis processing that relatively emphasizes the first detail component signal with respect to the first base component signal (step S20). Here, for example, the relative emphasizer 230 outputs the first detail component signal as a second detail component signal and the gradation compressor 231 outputs a second base component signal generated by performing the gradation compression processing on the first base component signal. In this regard, it is desirable that the gradation compression processing use the same parameter as that used in gradation compression processing for a typical endoscopic image.

Further, the processing device 200 combines the base component signal and the detail component signal (step S30). Here, for example, the combiner 240 performs the combining by multiplying the first base component signal and the first detail component signal outputted from the relative emphasizer 230 and outputs a combined image signal.

At the end, the processing device 200 generates an image signal for display on the basis of the combined image signal (step S40), outputs the image signal for display to the display device 300 (step S50), and terminates the image signal processing. Here, for example, the display image generator 250 generates the image signal for display on the basis of the combined image signal and outputs the image signal for display to the display device 300.

The processing device 200 performs the image signal processing shown in FIG. 2 in the above-described manner, thereby relatively emphasizing the detail component signal with respect to the base component signal, which makes it possible to obtain an endoscopic image having a higher visibility than ever before. In particular, gradation compression of only the base component signal results in maintaining the detail component signal, which contains a contrast component, without change. This allows for preventing deterioration of contrast attributed to the gradation compression processing to achieve a higher visibility than ever before. Further, the gradation compression processing uses the same parameter as typically used, which allows for reducing a change in color resulting from a difference in gradation compression processing. This allows for reducing a difference in impression resulting from a change in color and minimizing an influence on existing established pathognomy.

Further, the processing device 200 performs the image signal processing shown in FIG. 2, thereby approximating the base component signal to the image signal in accordance with the control parameter, which allows for adjusting a difference in impression from a typical endoscopic image. More specifically, when the base component signal is approximated to the image signal to become the very same as the image signal (for example, α=1), the detail component signal also becomes the same as the image signal. In this case, compressing only the base component signal by the relative emphasis processing means substantially the same as compressing the image signal as a whole. Accordingly, the relative emphasis processing performed by the relative emphasizer 230 is almost the same as typical gradation compression processing that is to be performed in accordance with a monitor performance or the like. In other words, the degree of the relative emphasis is reduced with the base component signal further approximated to the image signal, which approximates the image signal for display to an image signal of a typical endoscopic image and, consequently, reduces a difference in impression. Thus, a difference in impression from a typical endoscopic image can be adjusted by adjusting the control parameter. In particular, by virtue of using an alpha value as the control parameter, the impression can be minutely adjusted by finely adjusting the alpha value, which is applicable to even a slight difference in impression attributed to, for example, differences among individuals, or the like.

Therefore, the processing device 200 according to the present embodiment enables both improvement in visibility with respect to a typical endoscopic image and adjustment of a difference in impression from a typical endoscopic image at a high level.

Second Embodiment

Figure 6:
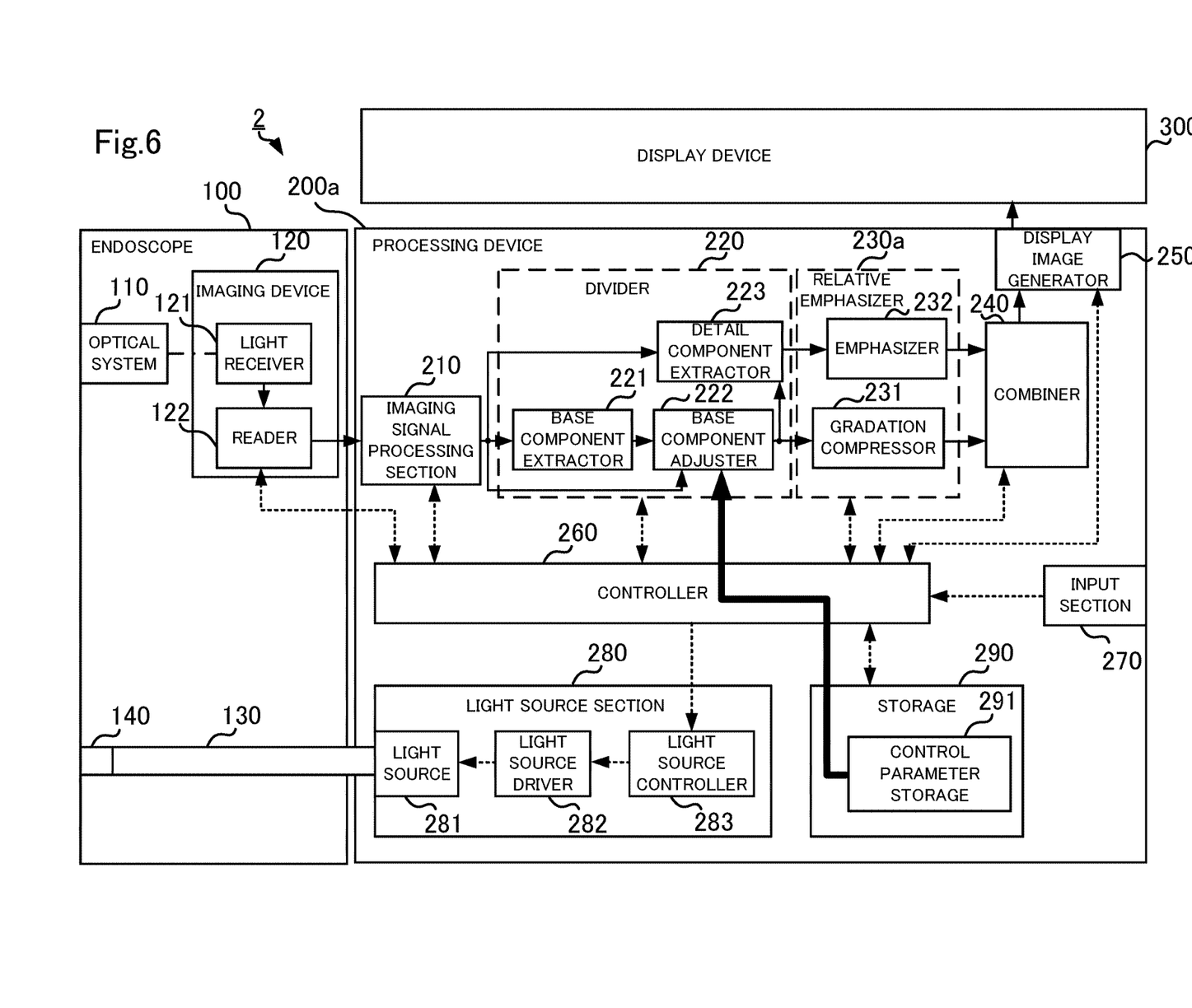
FIG. 6 shows an example of a configuration of an endoscope system 2 according to an exemplary embodiment.

FIG. 6 shows an example of a configuration of an endoscope system 2 according to the present embodiment. The endoscope system 2 shown in FIG. 6 is different from the endoscope system 1 in that the endoscope system 2 includes a processing device 200a in place of the processing device 200. Except for that, the endoscope system 2 is similar to the endoscope system 1 and the same reference signs are used to refer to the same components and a detailed description thereof will be omitted.

The processing device 200a is different from the processing device 200 in that the processing device 200a includes a relative emphasizer 230a in place of the relative emphasizer 230. The relative emphasizer 230a is different from the relative emphasizer 230 in that the relative emphasizer 230a performs the signal processing for relatively emphasizing a first detail component signal with respect to a first base component signal not only on a first base component signal but also on a first detail component signal. In more detail, the relative emphasizer 230a includes an emphasizer 232 in addition to the gradation compressor 231.

The emphasizer 232 generates a second detail component signal by performing emphasis processing on the first detail component signal received from the detail component extractor 223 and outputs the second detail component signal to the combiner 240. A method for the emphasis processing performed by the emphasizer 232 is not limited.

The emphasis processing may be, for example, gain-up processing performed by using a parameter and the parameter to be used may be calculated by a function dependent on a luminance value.

Similarly to the processing device 200, the processing device 200a also allows for improving visibility with respect to a typical endoscopic image and adjusting a difference in impression from the typical endoscopic image. Further, in addition to a reduction in deterioration of contrast resulting from not performing gradation compression of the detail signal component, i.e., an improvement in relative contrast with respect to a typical endoscopic image, the processing device 200a allows for an improvement in absolute contrast by emphasizing the detail signal component. Therefore, the processing device 200a according to the present embodiment allows for achieving a higher visibility than the processing device 200.

Third Embodiment

Figure 7:
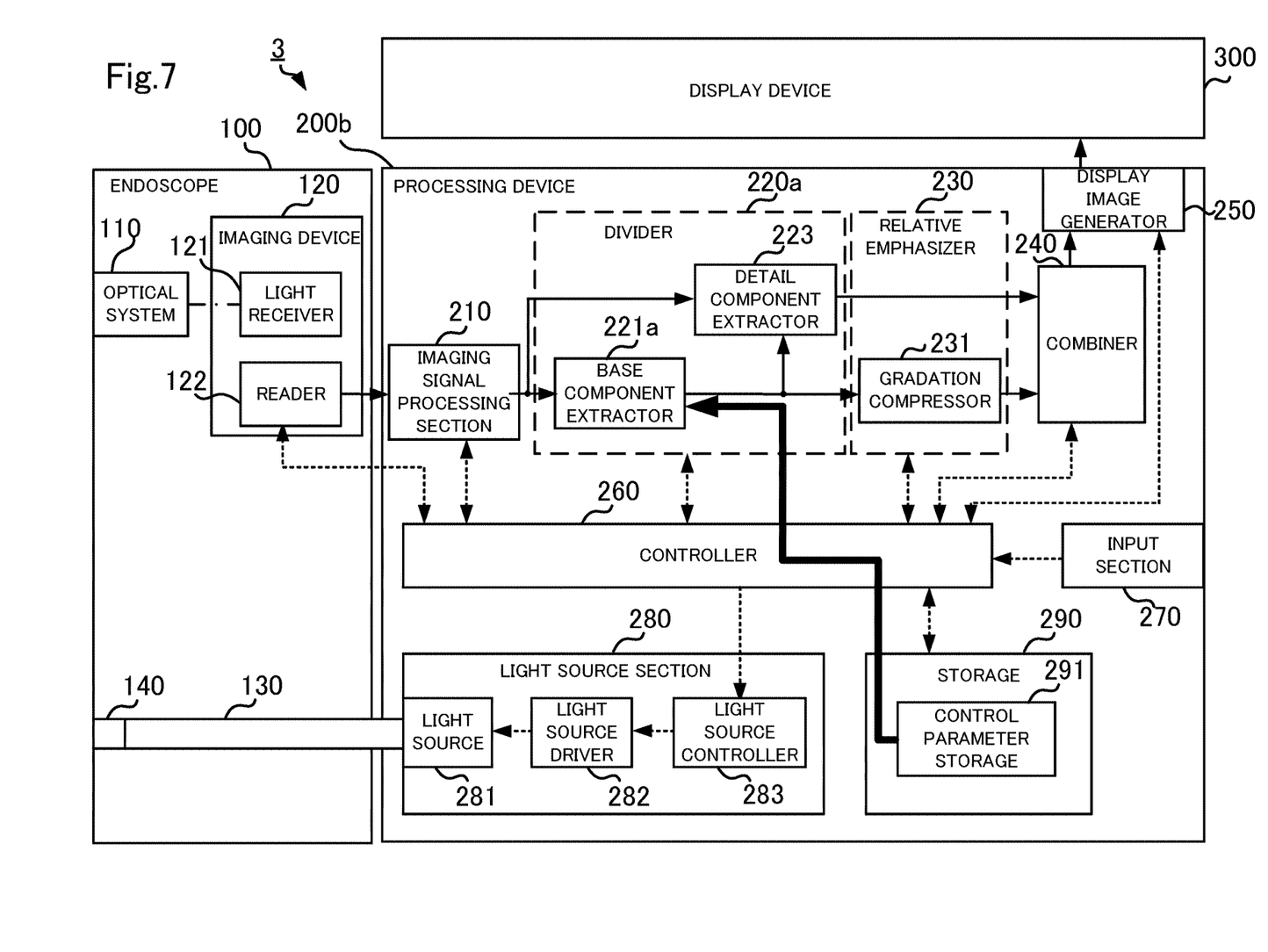
FIG. 7 shows an example of a configuration of an endoscope system 3 according to an exemplary embodiment.

FIG. 7 shows an example of a configuration of an endoscope system 3 according to the present embodiment. The endoscope system 3 shown in FIG. 7 is different from the endoscope system 1 in that the endoscope system 3 includes a processing device 200b in place of the processing device 200. Except for that, the endoscope system 3 is similar to the endoscope system 1 and the same reference signs are used to refer to the same components and a detailed description thereof will be omitted.

The processing device 200b is different from the processing device 200 in that the processing device 200b includes a divider 220a in place of the divider 220. The divider 220a is different from the divider 220 in that the divider 220a generates a first base component signal directly from an image signal instead of generating a first base component signal by blending an original base component signal generated from the image signal and the image signal. In more detail, the divider 220a includes a base component extractor 221a in place of the base component extractor 221 and the base component adjuster 222.

The base component extractor 221a is the same as the base component extractor 221 in that the base component extractor 221a generates a base component signal by extracting a base component from an image signal received from the imaging signal processing section 210. Further, regarding a method of extracting the base component, for example, an edge preserving smoothing filter such as a bilateral filter or an epsilon filter may be used, which is also the same as in the base component extractor 221. However, the base component extractor 221a is different in that the base component extractor 221a determines a filter in accordance with a control parameter and smooths the image signal with the determined filter.

The base component extractor 221a determines, for example, a kernel size and a filter coefficient in accordance with the control parameter. Further, a filter is selected from among a plurality of filters prepared in advance in accordance with the control parameter to determine a filter used in filtering processing. Accordingly, the degree of approximation of the first base component signal generated by the base component extractor 221a to the image signal can be adjusted by the control parameter.

Figure 8:
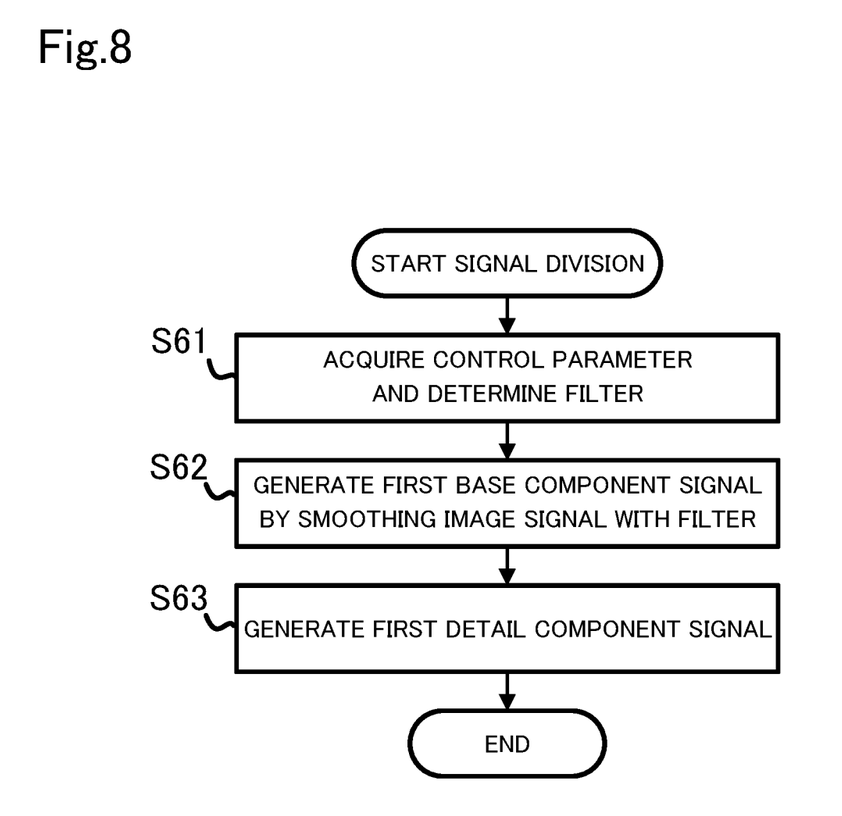
FIG. 8 is a flowchart of signal division processing according to an exemplary embodiment.

FIG. 8 is a flowchart of signal division processing according to the present embodiment. The processing device 200b also performs the image signal processing shown in FIG. 2. However, in the signal division processing of step S10, the processing device 200b performs signal division processing shown in FIG. 8 in place of the signal division processing shown in FIG. 3.

When the signal division processing shown in FIG. 8 is started, the processing device 200b first acquires a control parameter and determines a filter (step S61). Here, for example, the base component extractor 221a reads the control parameter from the control parameter storage 291 and determines the filter used in the filtering processing. It should be noted that the control parameter has been determined in advance in accordance with selection by an operator.

Next, the processing device 200b smooths the image signal with the filter to generate a first base component signal (step S62). Here, for example, the base component extractor 221a performs the filtering processing with the filter determined in step S61, thereby generating the first base component signal.

At the end, the processing device 200b generates a first detail component signal (step S63) and terminates the signal division processing. This processing is similar to the processing in step S14 shown in FIG. 3.

Similarly to the processing device 200, the processing device 200b also allows for improving visibility with respect to a typical endoscopic image and adjusting a difference in impression from the typical endoscopic image. Further, in the processing device 200b, the filter is changed in accordance with the control parameter to approximate the base component signal to the image signal. This makes it possible to obtain the above-described effects without the necessity of considerably changing a configuration of an existing processing device.

The above-described embodiments are intended to provide specific examples for facilitating understanding of the invention; therefore, the present invention is not limited to these embodiments. The image signal processing device, the image signal processing method, and the program may be modified or altered in a variety of manners without departing from the scope of claims.

FIG. 1, FIG. 6, and FIG. 7 each show an example where the relative emphasizer includes the gradation compressor 231; however, the relative emphasizer only has to relatively emphasize the detail component signal with respect to the base component signal and thus the configuration including the gradation compressor 231 is not limiting. The relative emphasizer only has to output the second base component signal and the second detail component signal by performing the signal processing for relatively emphasizing the first detail component signal with respect to the first base component signal on at least one of the first base component signal and the first detail component signal. In other words, the relative emphasizer only has to include at least one of the gradation compressor 231 and the emphasizer 232.

Further, FIG. 1, FIG. 6, and FIG. 7 each show an example where the processing device includes the light source section; however, the processing device does not necessarily include the light source section. The processing device may be connected to a light source device independent of the processing device and a light quantity control of the illumination light to be delivered to the endoscope 100 may be performed by controlling the light source device.

Further, FIG. 1, FIG. 6, and FIG. 7 each show an example where the processing device is an endoscope processor included in the endoscope system; however, the processing device is not limited to an endoscope processor. For example, the processing device may be an image signal processing device that performs image signal processing on an image signal of a microscopic image acquired with a microscope.

Further, FIG. 1, FIG. 6, and FIG. 7 each show an example where the control parameter is stored in advance in the control parameter storage 291 included in the processing device; however, the control parameter may be acquired from a unit outside the processing device, such as a cloud server on the Internet, if necessary.

Although it is not mentioned above, the processing for a base component signal and a detail component signal by the divider and the relative emphasizer may be performed on a color component basis. For example, the variety of processing may be performed with a base component signal and a detail component signal generated for each of color components of R, G, and B.

Further, each processing in the flowchart shown in each of FIG. 2, FIG. 3, and FIG. 8 may be implemented by hardware processing or may be implemented by software processing based on execution of a program developed on a memory.

Further, the image signal processing device may include a configuration in addition to the configurations shown in FIG. 1, FIG. 6, and FIG. 7. The image signal processing device may include, for example, a brightness corrector between the divider and the relative emphasizer. The brightness corrector may perform processing for correcting a luminance value on a first base component signal outputted from the divider to increase brightness of an image.

Further, in each of the image signal processing devices shown in FIG. 1, FIG. 6, and FIG. 7, the gradation compressor exemplarily compresses the first base component signal; however, a signal to be compressed by the gradation compressor is not limited to the first base component signal. For example, the relative emphasizer may include a gradation compressor that performs gradation compression processing on any one of an image signal, an original base component signal, or a first base component signal to generate a second base component signal. In this case, the gradation compressor may perform gradation compression signal processing on any one of the image signal, the original base component signal, or the first base component signal in accordance with settings set by a user. For example, in a case where it is not necessary to adjust the degree of emphasis, the compression processing may be performed on the original base component signal. In a case where visibility is improved while adjusting a difference in impression from a typical image, the compression processing may be performed on the first base component signal. This enables a user to selectively apply image processing for improving the visibility of a disease in accordance with situations as appropriate.

What is claimed is:

1. An image signal processing device comprising:
a processor and a memory, the processor being configured to perform the following steps:
generate an original base component signal by extracting a base component from an image signal;
generate a first base component signal by performing weighted average processing on the image signal and the original base component signal using a base component adjuster;
generate a first detail component signal by extracting a detail component from the image signal based on the first base component signal;
output a second base component signal and a second detail component signal by performing signal processing on at least one of the first base component signal and the first detail component signal, the signal processing emphasizing the first detail component signal to generate the second detail component signal, and the signal processing performing gradation compression processing on the first base component signal to generate the second base component signal;
generate a combined image signal by combining the second base component signal and the second detail component signal; and
store a plurality of control parameters regarding similarity between the image signal and the first base component signal, wherein
the base component adjuster is configured to:
acquire a control parameter selected from among the stored plurality of control parameters; and
generate the first base component signal by performing the weighted average processing by using a weight coefficient determined in accordance with the control parameter.

2. The image signal processing device according to claim 1, wherein:
the weighted average processing is alpha blend processing, and
the control parameter is an alpha value used for the alpha blend processing.

3. The image signal processing device according to claim 1, the image signal comprising:
the base component that is less correlated with visual perception than the detail component; and
the detail component that is more correlated with visual perception than the base component.

4. An image signal processing device comprising:
a processor and a memory, the processor being configured to:
divide an image signal into a first base component signal and a first detail component signal in accordance with a control parameter;
output the first base component signal and the first detail component signal;
output a second base component signal and a second detail component signal by performing signal processing on at least one of the first base component signal and the first detail component signal, the signal processing relatively emphasizing the first detail component signal to generate the second detail component signal, and the signal processing performing gradation compression processing on the first base component signal to generate the second base component signal;
generate a combined image signal by combining the second base component signal and the second detail component signal; and
store a plurality of control parameters regarding similarity between the image signal and the first base component signal, wherein:
the processor is configured to divide the image signal into the first base component signal and the first detail component signal in accordance with the control parameter selected from among the stored plurality of control parameters and output the first base component signal and the first detail component signal.

5. The image signal processing device according to claim 4, that the processor is configured to generate an original base component signal by extracting a base component from the image signal;
generate the first base component signal by performing weighted average processing on the image signal and the original base component signal by using a weight coefficient determined in accordance with the control parameter; and generate the first detail component signal by extracting a detail component from the image signal based on the first base component signal.

6. The image signal processing device according to claim 4, the processor is configured to:

generate the first base component signal by smoothing the image signal with a filter determined in accordance with the control parameter; and generate the first detail component signal by extracting a detail component from the image signal based on the first base component signal.

7. An image signal processing device comprising a processor and a memory, the processor configured to:

generate an original base component signal by extracting a base component from an image signal;

generate a first base component signal by performing weighted average processing on the image signal and the original base component signal;

generate a first detail component signal by extracting a detail component from the image signal based on the first base component signal;

output a second base component signal and a second detail component signal by performing signal processing on at least one of the first base component signal and the first detail component signal, the signal processing emphasizing the first detail component signal with respect to the first base component signal to generate the second detail component signal, and the signal processing performing gradation compression processing on the first base component signal to generate the second base component signal;

generate a combined image signal by combining the second base component signal and the second detail component signal; and store a plurality of control parameters regarding similarity between the image signal and the first base component signal, wherein generate the first base component signal by acquiring a control parameter selected from among the stored plurality of control parameters and performing the weighted average processing by using a weight coefficient determined in accordance with the control parameter, and generate the second base component signal by performing gradation compression processing on any one of the image signal, the original base component signal, or the first base component signal.

8. A computer-implemented image signal processing method comprising:

generating an original base component signal by extracting a base component from an image signal;

generating a first base component signal by performing, on the image signal and the original base component signal, weighted average processing by using a weight coefficient determined in accordance with a selected control parameter;

generating a first detail component signal by extracting a detail component from the image signal based on the image signal and the first base component signal;

outputting a second base component signal and a second detail component signal by performing signal processing on at least one of the first base component signal and the first detail component signal, the signal processing emphasizing the first detail component signal to generate the second detail component signal, and the signal processing performing gradation compression processing on the first base component signal to generate the second base component signal; and generating a combined image signal by combining the second base component signal and the second detail component signal.

9. A non-transitory computer-implemented program configured to execute the following steps:

generating an original base component signal by extracting a base component from an image signal;

generating a first base component signal by performing, on the image signal and the original base component signal, weighted average processing by using a weight coefficient determined in accordance with a selected control parameter;

generating a first detail component signal by extracting a detail component from the image signal based on the image signal and the first base component signal;

outputting a second base component signal and a second detail component signal by performing signal processing on at least one of the first base component signal and the first detail component signal, the signal processing emphasizing the first detail component signal to generate the second detail component signal, and the signal processing performing gradation compression processing on the first base component signal to generate the second base component signal; and generating a combined image signal by combining the second base component signal and the second detail component signal.

* * * * *